United States Patent [19]
Burke et al.

[11] Patent Number: 5,612,041
[45] Date of Patent: Mar. 18, 1997

[54] RECOMBINANT HERPES SIMPLEX GD VACCINE

[75] Inventors: Rae L. Burke; Mickey S. Urdea; Pablo D. T. Valenzuela, all of San Francisco, Calif.

[73] Assignee: Chiron Corporation, Emeryville, Calif.

[21] Appl. No.: 312,666

[22] Filed: Sep. 27, 1994

Related U.S. Application Data

[63] Continuation of Ser. No. 991,703, Dec. 17, 1992, abandoned, which is a continuation of Ser. No. 477,027, Feb. 8, 1990, abandoned, which is a continuation of Ser. No. 921,214, Oct. 20, 1986, abandoned, which is a continuation-in-part of Ser. No. 631,669, Apr. 17, 1984, Pat. No. 4,618,578.

[51] Int. Cl.$^6$ .................................................. A61K 39/245
[52] U.S. Cl. .................................. 424/231.1; 424/186.1; 424/279.1; 435/69.3; 935/65
[58] Field of Search ........................... 424/231.1, 186.1, 424/279.1; 435/69.1, 69.3; 935/65

[56] References Cited

U.S. PATENT DOCUMENTS

| | | | |
|---|---|---|---|
| 4,317,811 | 3/1982 | Bertland et al. | 424/231.1 |
| 4,374,127 | 2/1983 | Larson et al. | 421/231.1 |
| 4,618,578 | 10/1986 | Burke et al. | 435/69.3 |
| 4,642,333 | 2/1987 | Person | 530/350 |
| 4,661,349 | 4/1987 | Kino et al. | 424/231.1 |
| 4,724,146 | 2/1988 | Kino et al. | 424/231.1 |
| 4,762,708 | 8/1988 | Cohen et al. | 424/186.1 |
| 4,818,694 | 4/1989 | Watson et al. | 435/69.3 |
| 4,855,224 | 9/1989 | Berman et al. | 435/5 |
| 4,870,008 | 9/1989 | Brake | 435/69.4 |
| 4,891,315 | 8/1989 | Watson et al. | 435/69.3 |

FOREIGN PATENT DOCUMENTS

| | | |
|---|---|---|
| 0133063 | 2/1985 | European Pat. Off. . |
| 139417 | 7/1989 | European Pat. Off. . |

OTHER PUBLICATIONS

Hilfenhaus et al., *Devel. Biol. Standard.* (1982) 52:321–331.
Watson et al., *Science* (1982) 218:381–384.
Weis et al., *Nature* (1983) 302:72–74.
Berman et al., *Science* (1983) 222:524–527.
Lasky et al., *Biotechnology* (Jun. 1984) pp. 527–532.
Cohen et al., *J. Virol.,* (1984) 49:102–108.
Dundarov et al., *Devel. Biol. Standard.* (1982) 52:351–357.
Skinner et al., *Devel. Biol. Standard.* (1982) 52:333–344.
Eberle et al., *J. Infect. Dis.* (1983) 148(3):436–444.
Marsden et al., *J. Virol.* (1978) 28(2):624–642.
Ruyechan et al., *J. Virol.* (1979) 29(2):677–697.
Skare et al., *Virology* (1977) 76:581–595.
Roizman et al., *Ann. Rev. Genetics* (1979) 13:25–57.
Berman et al., *Science* (1985) 227:1490–1492.
Cappel et al., *J. Medical. Virol.* (1985) 16:137–145.
Pellet et al., *J. Virol.* (1985) 53(1):243–253.
Bzik et al., *Virology* (1984) 133:301–314.
Chan *Immunology* (1983) 49:343–352.
Roizman et al., *Develop. Biol. Stand.* (1982) 52:287–304.
Cohen, J. 1994. Science, vol. 264, pp. 503–506.
Straus, S. E. et al. 1985. Annals of Internal Medicine, vol. 103, pp. 404–419.
Sabin, A. B. 1981. JAMA, vol. 246, pp. 236–241.
Watson et al. Science vol. 218 1982 p. 381.
Berman et al. Science vol. 227 Mar. 1985, p. 1490.
Brake et al. Proc. Nat. Acad. Sci vol. 81 pp. 4642–4646 Aug. 1984.

*Primary Examiner*—Mary E. Mosher
*Attorney, Agent, or Firm*—Barbara G. McClung; Roberta L. Robins; Robert P. Blackburn

[57] ABSTRACT

Vaccines against Herpes Simplex virus containing recombinant polypeptides which are cross-reactive with glycoprotein D of the virus, methods for their production using recombinant DNA techniques in yeast, and methods for the use of the vaccine are provided. *E. coli* strains HB101 containing plasmids pYHS 109 and pYHS118 were deposited at the American Type Culture Collection on Jul. 11, 1984, and granted accession nos. 39762 and 39763, respectively.

5 Claims, 5 Drawing Sheets

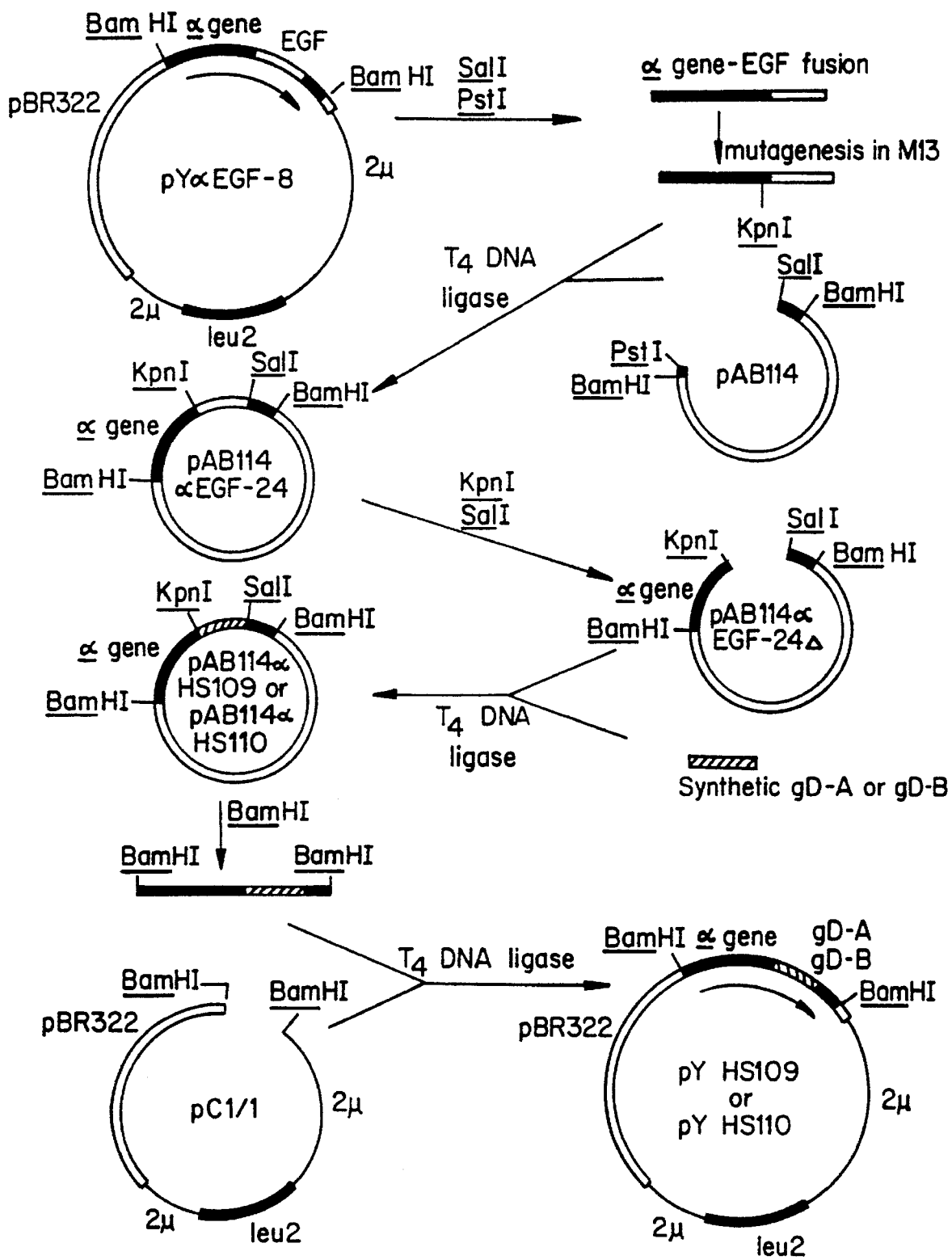
FIG._1.

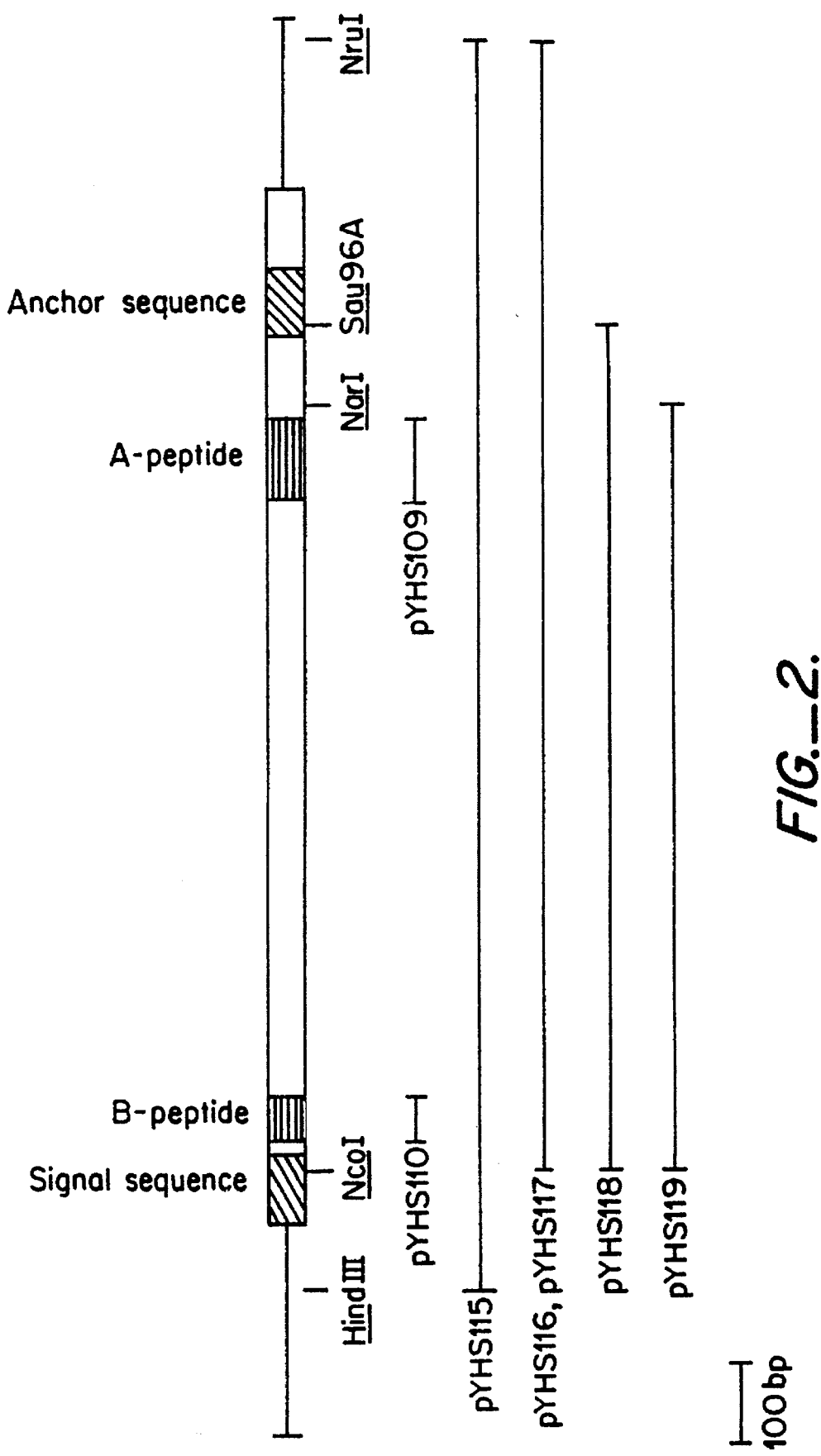
FIG._2.

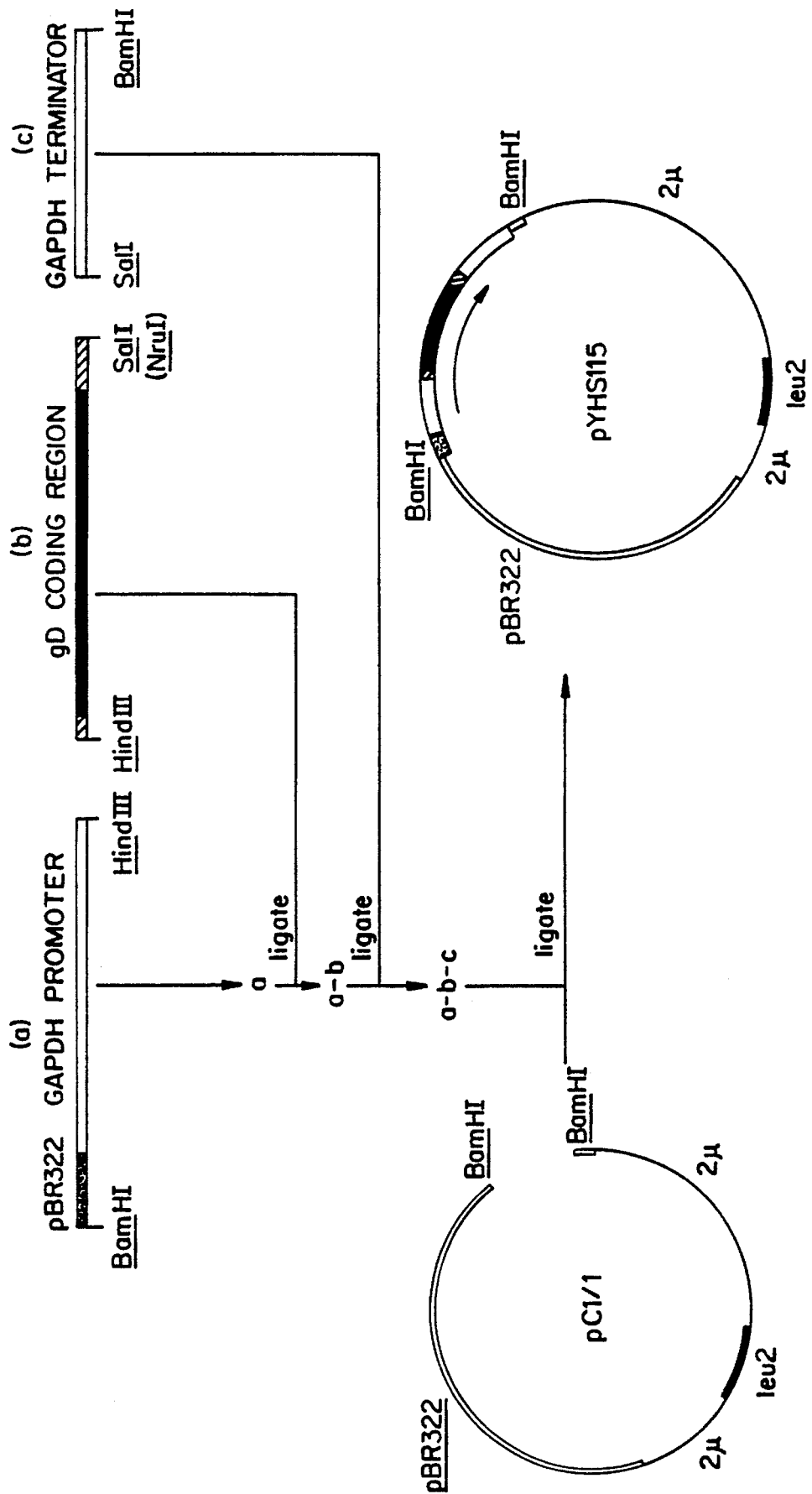
FIG._3.

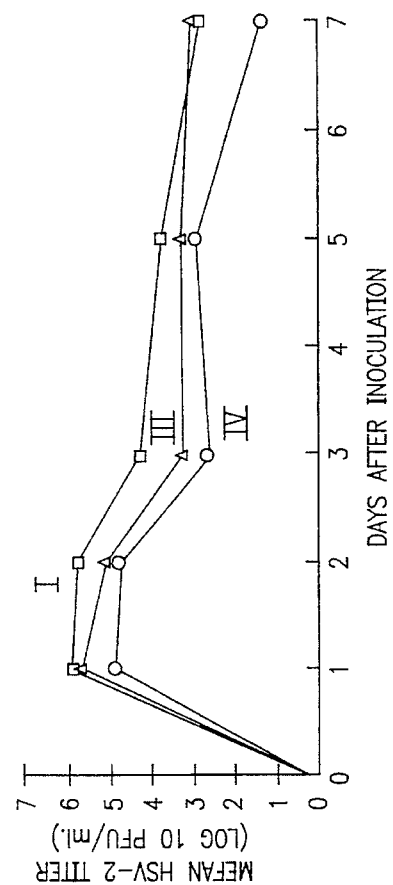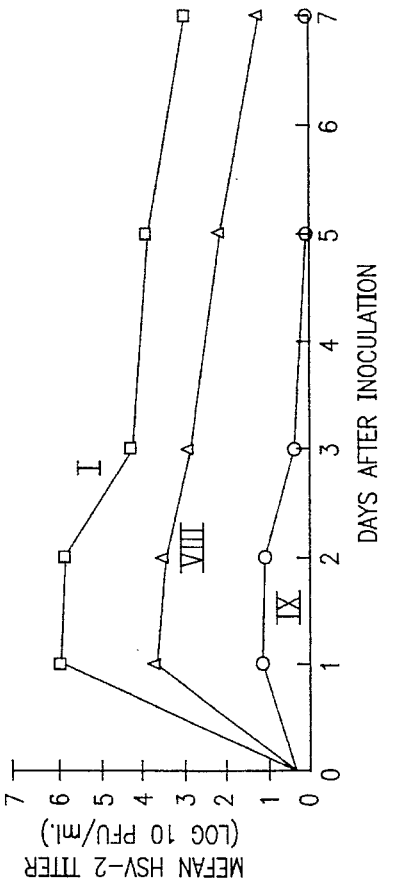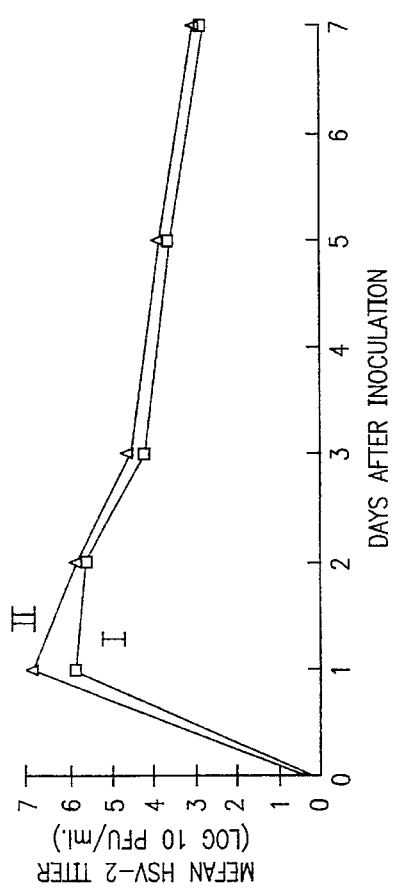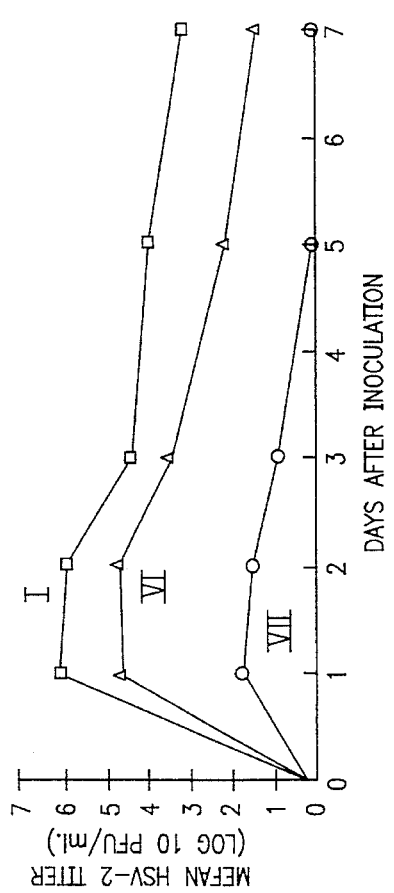
FIG. 5A  B. CONTROL GROUPS
FIG. 5B  B. CLONED HSV-1 GLYCOPROTEINS
FIG. 5C  C. TOTAL HSV-1 GLYCOPROTEINS
FIG. 5D  D. TOTAL HSV-2 GLYCOPROTEINS

RECOMBINANT HERPES SIMPLEX GD VACCINE

This application is a continuation of application Ser. No. 07/991,703, filed 17 Dec. 1992, now abandoned, which is a continuation of application Ser. No. 07/477,027, filed 8 Feb. 1990, now abandoned, which is a continuation of application Ser. No. 06/921,214, filed 20 Oct. 1986, now abandoned, which is a continuation-in-part of application Ser. No. 06/631,669, filed 17 Apr. 1984, which is now U.S. Pat. No. 4,618,578.

BACKGROUND OF THE INVENTION

1. Field of the Invention

The herpes viruses include the Herpes Simplex viruses, comprising two closely related variants designated types 1 (HSV-1) and 2 (HSV-2). HSV-1 and HSV-2 are responsible for a variety of human diseases, such as skin infections genital herpes, viral encephalitis, and tile like.

The Herpes Simplex virus is a double stranded DNA virus having a genome of about 150 to 160 kbp packaged within an icosahedral nucleocapsid enveloped in a membrane. The membrane includes a number of virus-specific glycoproteins, the most abundant of which are gB, gC, gD and gE, where gB and gD are cross-reactive between types 1 and 2.

It is a matter of great medical and scientific interest to provide safe and effective human vaccines against both HSV-1 and HSV-2. One promising approach has been the use of isolated glycoproteins which have been shown to provide protection when injected into mice subsequently challenged with live virus. One limitation on the use of such "subunit" vaccines, however, has been the difficulty in obtaining sufficient amounts of the glycoproteins. Heretofore, such glycoproteins have been obtained primarily from membranes isolated from a viral culture. The problems associated with large scale culturing of these pathogens and the difficulty in isolating the glycoproteins from the viral genome have substantially precluded the use of glycoprotein vaccines.

It would therefore be desirable to provide a safe and efficient method for the large-scale production of Herpes Simplex glycoproteins suitable for use as human vaccines. In particular, it would be desirable to provide for the production of a polypeptide having an amino acid sequence similar to glycoprotein D, or a portion thereof, which polypeptide can elicit an immune response against both HSV-1 and HSV-2. The vaccines utilizing this recombinant polypeptide could be used for the prophylaxis and treatment of Herpes Simplex virus infections in humans.

2. Description of the Prior Art

Subunit vaccines extracted from chick embryo cells infected with HSV-1 or HSV-2 are described in U.S. Pat. Nos. 4,317,811 and 4,374,127. See also, Hilfenhaus et al. (1982) Develop. Biol. Standard 52:321–331, where the preparation of a subunit vaccine from a particular HSV-1 strain (BW3) is described. Roizman et al. (1982) Develop. Biol. Standard 55:287–304, describe the preparation of non-virulent HSV-1×HSV-Z recombinants and deletion mutants which are shown to be effective in immunizing mice. Watson et al. (1982) Science 218:381–384 describe the cloning and low level expression of the HSV-1 gD gene in *E. coli*, as well as expression of a cloned fragment by injection into the nuclei of frog oocytes. They also present the nucleotide sequence for the gD gene. Weis et al. (1983) Nature 302:72–74 report higher level expression of gD in *E. coli*. This polypeptide elicits neutralizing antibodies in rabbits. Betman et al. (1983) Science 222:524–527 report the expression of glycoprotein D in mammalian cell culture. Lasky et al., Biotechnology, June 1984. pp. 527–532 report the use of this glycoprotein D for the immunization of mice. Cohen et al. (1984) J. Virol. 49:102–108 reports the localization and chemical synthesis of a particular antigenic determinant of gD, contained within residues 8–23 of the mature protein.

"Therapeutic" use of preparations of membrane proteins from HSV-infected cells for post-infection vaccine in humans are reported by Dundarov, S., et al., Dev. Biol. Standard (1982) 52:351–357: and Skinner, G. R. B., et al. ibid (1982) 52:333–344.

SUMMARY OF THE INVENTION

Novel vaccines and therapeutic compositions against Herpes Simplex Virus Types 1 and 2 and methods for their production and use are provided. These vaccines employ virus specific polypeptides produced by recombinant DNA technology. Particularly, recombinant HSV gD produced in modified mammalian and yeast hosts was employed as vaccines. Accordingly, one aspect of the invention provides a vaccine against Herpes Simplex virus. This vaccine contains a recombinant polypeptide, which is synthesized in yeast, and which is immunologically cross-reactive with glycoprotein D of Herpes Simplex virus. The vaccine contains an amount of the polypeptide which produces an immune response in a mammalian host. Another aspect of the invention provides methods for preparing vaccines against Herpes Simplex virus, wherein an immunogenically active polypeptide which is cross-reactive with glycoprotein D is synthesized in yeast, isolated, and formulated into a vaccine. Finally, another aspect of the invention provides methods for immunizing a mammal against Herpes Simplex virus wherein the mammal is vaccinated with the recombinant glycoprotein D vaccine described above.

BRIEF DESCRIPTION OF THE DRAWINGS

FIG. 1 represents the construction of plasmids pYHS109 and pYHS110 which carry synthetic sequences gD-A and gD-B, respectively, as described in the Experimental section hereinafter.

FIG. 2 is a partial restriction map of the gD region which notes the location of all the gD sequences inserted into yeast expression vectors, as described in the Experimental Section hereinafter.

FIG. 3 represents the construction of plasmid pYHS115 which carries the naturally occurring gD gene of HSV-1 strain Patton, under the transcriptional control of the GAPDH promoter and terminator, as described in the Experimental section hereinafter.

FIG. 5A, 5B, 5C, and 5D are graphs showing the effect of vaccines on the virologic course of primary genital herpes in female guinea pigs intravaginally inoculated with HSV-2.

DESCRIPTION OF THE SPECIFIC EMBODIMENTS

Figure 4B:
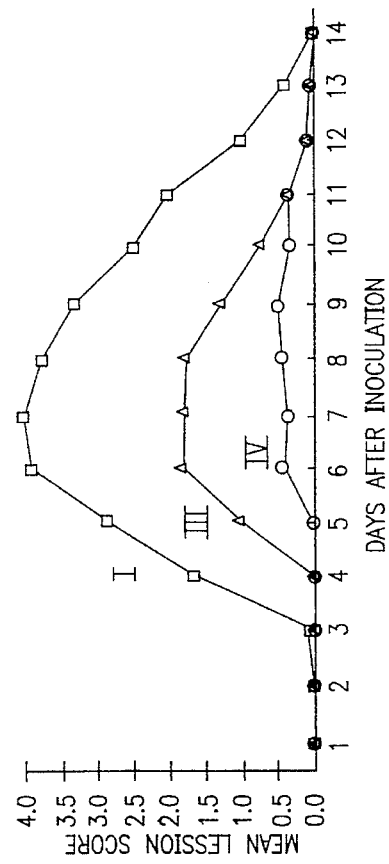
FIG. 4A, 4B, 4C, and 4D are graphs showing the effect of vaccines on the clinical course of external genital skin disease in female guinea pigs intravaginally inoculated with HSV-2.

Polypeptides which are immunologically cross-reactive with naturally occurring glycoprotein D are produced in yeast by recombinant DNA methodology. Production in yeast allows the advantages associated with eukaryotic hosts, e.g., post-translational modification and secretion, without the problems associated with maintaining a mammalian cell culture. The recombinant polypeptides of the present invention may be produced from relatively short synthetic DNA fragments encoding for at least about nine amino acids to provide haptens useful for eliciting an immune response specific for gD, e.g., for use in vaccine production. The cloned DNA fragments (or the RNA produced therefrom) may also find use as hybridization probes in a variety of applications. Alternatively, much longer DNA fragments, either synthetic or natural, may be used to produce larger recombinant polypeptides for use as vaccines, immunogens, immunological reagents, and the like. The recombinant peptides of the present invention will find particular use in the preparation of vaccines against infection by Herpes Simplex virus.

The recombinant glycoprotein D (gD) DNA fragments of the present invention may be of natural or synthetic origins. The natural gD gene of HSV-1 is located on the viral genome between the short internal repeat ($IR_S$) sequence and short terminal repeat ($TR_S$) sequence at the 3'-end thereof. Coding for the mature protein is found on an approximately 1.6 kbp fragment located on a 2.9 kbp SacI restriction fragment of the genome. The entire coding region for the mature protein is located within a HindIII-NruI fragment of the 2.9 kbp SacI fragment. The naturally occurring gD gene may be employed with or without modification. Regions of the gene may be deleted and/or joined to other DNA fragments as desired. The preparation, cloning and expression of particular fragments of the naturally occurring gD gene are described in detail in the Experimental section hereinafter.

Synthetic gD sequences will also find use, either alone or in combination with the naturally occurring sequences. Coding for the synthetic sequences may be based on published nucleotide sequences for gD found in the literature. See, Watson et al. (1982), supra. The synthetic fragments will be sufficiently long to code for at least nine contiguous amino acids with a maximum length equal to that of the naturally occurring gene or longer. When preparing recombinant polypeptides for use as immunological reagents or as vaccines, it is usually desirable that the nucleotide sequence code for an oligopeptide corresponding to an epitopic site of the natural gD protein. Often, such epitopic sites may be predicted by employing the folding rules of Chou and Fasman (1974) Biochemistry 13:211–222, in conjunction with an analysis of hydrophobic and hydrophilic regions of the protein (Hopp and Woods, (1981), Proc. Natl. Acad. Sci. U.S.A. 78:3824–3828). In particular, it has been found that polypeptides corresponding to amino acids 253–283 and 8–23 in the mature naturally occurring gD protein will cross-react with antisera raised against the natural gD protein.

A number of techniques are available for synthesizing short single-stranded DNA fragments, e.g., the phosphoramidite method described by Beaucage and Carruthers (1981) Tetrahedron Lett. 22:1859–1862. Short fragments having a length of about 40 bases or less may be synthesized as a continuous single-stranded fragment. The complementary strand may also be synthesized and the two strands annealed under appropriate conditions. Alternatively, the complementary strand may be added using DNA polymerase with an appropriate primer sequence.

The synthesis of longer fragments exceeding 100 base pairs is typically accomplished by the preparation of a series of single-stranded DNA fragments including from about 10 to 100 bases, usually from about 15 to 60 bases. The sequences of such fragments are selected so that when the fragments are brought together under annealing conditions, a double stranded fragment having the desired nucleotide sequence is produced. When devising such synthetic nucleotide sequences, the sequences of the individual single-stranded DNA fragments are examined to assure that annealing of unmatched segments is avoided. In this way, base pairing occurs only between those segments which are intended to be annealed in the resulting double stranded DNA fragment. Undesired base pairing may usually be avoided by altering one nucleotide (usually the third nucleotide) in preselected ones of the codons.

When preparing synthetic gD DNA fragments, it may sometimes be desirable to modify the reported nucleotide sequence. For example, it will usually be preferred to use codons which are preferentially recognized by the intended yeast host. Specifically, such codons are those which appear at high frequency in the structural genes encoding for the yeast glycolytic enzymes. The nucleotide sequence will usually comprise at least 50% preferred yeast codons, more usually at least 60%, and preferably at least 75%. In some instances, it may be desirable to further alter the nucleotide sequence to create or remove restriction sites or to substitute one or more amino acids in the resulting polypeptide. Such changes may be made to enhance the immunogenicity of the polypeptide, facilitate conjugating the polypeptide to a carrier protein, or the like, etc. It may also be desirable at times to add amino acids to the N-terminus or C-terminus of the polypeptide, where such additional amino acids may provide for a desired result.

The DNA fragments coding for a desired gD fragment will be incorporated in DNA constructs capable of self-replication and expression in yeast. Such DNA constructs will include a replication system recognized by the yeast host, the gD DNA fragment encoding the desired polypeptide product, transcriptional and translational initiation regulatory sequences joined to the 5'-end of the gD sequence, and transcriptional and translational termination regulatory sequences joined to the 3'-end of the gD sequence.

The transcriptional regulatory sequences will include a promoter, which may be the promoter associated with the secretory leader and processing signal sequence. Other promoters may also find use, particularly those involved with the enzymes in a yeast glycolytic pathway, such as the promoters for alcohol dehydrogenase, glyceraldehyde-3-phosphate dehydrogenase (GAPDH), pyruvate kinase, triose phosphate isomerase, phosphoglucoisomerase, phosphofructokinase, and the like. By employing these promoters with other regulatory sequences, such as enhancers, operators, and the like, and using a host having an intact regulatory system, one can regulate the expression of the gD polypeptide product by varying the carbon source, e.g., replacing glucose with galactose; varying the concentration of a nutrient, e.g., phosphate, or changing the temperature with a temperature sensitive promotor or regulatory system.

The transcriptional termination regulatory sequence will include a terminator, preferably a terminator balanced with the promoter to provide for proper transcription. Conveniently, the terminator which is naturally found with the promoter may be employed. The remaining sequences in the construct, including the replication systems for both yeast, e.g., 2μ plasmid and bacteria, e.g., Col El, are well known and amply described in the literature.

Enhanced yields of shorter polypeptides may be obtained by employing DNA constructs which include a secretory leader and processing signal sequence to effect secretion and post-translational modification of the gene product in yeast. The upper size limit on the secreted polypeptides is not fixed, although they will usually be below 40 kilodaltons, more usually below about 30 kilodaltons. Moreover, size is not the only determinative criterion as hydrophobic peptides may be more readily secreted than non-hydrophobic peptides. The secretory leader and processing signal sequences will normally be derived from naturally occurring DNA sequences in yeast which provide for secretion of a polypeptide. Such polypeptides which are naturally secreted by yeast include α-factor, a-factor, acid phosphatase, and the like. If desired, the naturally occurring sequence may be modified, for example, by reducing the number of lys-arg pairs which define the processing site (while retaining at least one pair), or by reducing the length of the secretory leader sequence (while retaining sufficient length to provide for secretion), or by introducing point mutations, deletions or other modifications which facilitate manipulation, e.g., introducing restriction recognition sites. Conveniently, the secretory leader and processing signal sequence may be joined to the gD DNA fragment by providing appropriate cohesive ends on the gD fragment, by use of appropriate adaptor molecules, or a combination of both.

Recombinant polypeptides of the present invention may also be produced intracellularly as follows. After the transformed cell culture has reached a high density, the cells will be separated, typically by centrifugation, lysed, and the gD polypeptides isolated by various techniques, such as extraction, affinity chromatography, electrophoresis, dialysis and combinations thereof.

The recombinant polypeptides of the present invention, and fragments thereof, may be employed in a variety of ways. The polypeptides can be employed both as labeled and unlabeled reagents in various immunoassays, bioassays, and the like, for the detection of HSV or antibodies to HSV. Suitable labels include radionuclides, enzymes, fluorescers, chemiluminescers, enzyme substrates or co-factors, enzyme inhibitors, particles, dyes, and the like. Such labeled reagents may be used in a variety of well known assays, such as radioimmunoassays, enzyme immunoassays, e.g., ELISA, fluorescent immunoassays, and the like. See, for example, U.S. Pat. Nos. 3,766,162; 3,791,932; 3,817,837; 3,996,345; and 4,233,402.

Polypeptides of the present invention may also find use in vaccines against herpes. These vaccines will be of particular use for the prevention and alleviation of diseases in humans caused by Herpes Simplex virus. The larger polypeptides, having a molecular weight exceeding about 5,000 daltons, may be used without further modification. The smaller haptens, however, should be conjugated to an appropriate immunogenic carrier in order to elicit the desired immune response. Suitable immunogenic carriers include tetanus toxoid. It will also be possible to link short DNA fragments expressing the gD polypeptides to genes expressing proteins from other pathogenic organisms or viruses. In this way, the resulting fused proteins may provide immunity for more than one disease. In preparing a vaccine, the polypeptides will normally be incorporated in a physiologically acceptable medium, such as water, saline, phosphate buffered saline, etc., and may be employed with a physiologically acceptable adjuvant. e.g., aluminum hydroxide, muramyl dipeptide derivatives and the like. The vaccine may be delivered in liposomes and/or in conjunction with immunomodulators like interleukin 2. The vaccine may be administered intravenously, intraarterially, subcutaneously, intraperitoneally, or the like. It may be advantageous to administer split doses of vaccines which may be administered by the same or different routes. The amount of immunogen employed per dose will be about 5 to 10 μg, if liquid, in a volume of about 0.25 to 1 ml, and may be administered repeatedly at two to four week intervals, usually not more than two to three times. The vaccine may be administered prior to an initial course of Herpes Simplex virus infection, as well as subsequent to the infection.

The following examples which are indicative of the utility of the vaccine for use in humans, are offered by way of illustration and not by way of limitation.

EXPERIMENTAL

I. Materials and Methods

The HSV-1 strain Patton and HSV-2 strain 333 viable stocks are available from Dr. Richard Hyman, Hershey Medical Center, Hershey, Pa. These viruses can be propagated in Vero cells available from Dr. Evelyn Linnette, Viro Labs, Emeryville, Calif., or from the American Type Tissue Culture Laboratory, the propagation being performed in accordance with standard procedures. A library of HSV-1 Patton EcoRI DNA fragments (Kudler et al. 1983 Virology 124:86–99) cloned in the EcoRI site of the plasmid pACYC184 (Chang and Cohen, J. Bacteriology (1978) 134:1141) can be obtained from Dr. Hyman or be independently prepared in accordance with conventional techniques. Two HSV-2 333 clones can also be obtained from Dr. Hyman, namely the HindIII fragments H and L inserted into the HindIII site of pBR322 (Sutcliffe, Nucleic Acids Research (1978) 5:2721).

I.A. Cloning.

All DNA manipulations were done according to standard procedures. See, Maniatis et al. Molecular Cloning, CSH (1982). Restriction enzymes, T4DNA ligase, E. coli, DNA polymerase I Klenow fragment, and other biological reagents were purchased from Bethesda Research Laboratories or other indicated commercial suppliers and used according to the manufacturer's directions. Double-stranded DNA fragments were separated on 1% agarose gels and isolated by electroelution.

I.B. ELISA Assay

The concentration of gD protein in chinese hamster ovary (CHO) cell conditioned medium was measured by an indirect enzyme-linked immunosorbent assay (ELISA) using a preparation of purified recombinant gD as a standard. Aliquots of 8D2, a gD-specific monoclonal antibody (Rector et al., Infect. and Immun. (1982) 38:168–174), diluted 1:1000 in PBS were adsorbed to the wells of a 96-well polyvinyl chloride plate by incubation for 1 hr at room temperature. Excess antibody was removed by 3 washes with phosphate buffered saline (PBS)-5% goat serum (GS). 50 μl aliquots of media samples or the gD protein standard diluted in PBS+ 1% GS were added to the wells and incubated for 1 hr at room temperature. The plates were then washed 3 times with PBS+1% GS and followed by a third 1 hr incubation with 50 μl of rabbit anti-HSV-1 polyclonal antibody diluted 1:100 in the same buffer. Excess secondary antibody was removed by 3 washes with PBS+1% GS. Finally, 50 μl of goat anti-rabbit horseradish peroxidase-conjugated antibody diluted 1:500 in PBS+1% GS, followed by 8 washes with PBS and then developed with 50 μl of 2,2'-azido-di-[3-ethylbenzthioazoline sulfonate] at a concentration of 1 mg/ml in 0.1M citric acid, pH 4.0, 0.003% $H_2O_2$. The color reaction was stopped after 5 minutes by the addition of 50 μl of 10% sodium dodecyl sulphate (SDS) and the absorbance was read at 414 nm in a microtiter plate reader.

I.C. Yeast transformation

Yeast were transformed (Hinnen et al. Proc. Natl. Acad. Sci. 75:1919, 1978) and grown using a variety of media including selective medium (yeast nitrogen base without leucine); YEPD medium, containing 1% (w/v) yeast estract, 2% (w/v) peptone and 2% (w/v) glucose, and others as appropriate and/or detailed below. Plating medium contained 2% (w/v) agar and for transformation 3% top agar.

II. Yeast

II.A. Construction of yeast expression vectors containing synthetic DNA fragments coding for polypeptides A and B of the gD1 gene.

Nucleotide seguences designated gD-A and gD-B based on portions of the amino acid sequence for glycoprotein D of HSV-1 reported by Watson et al. (1982) Science 218:381–384, and employing preferred yeast codohs, were devised. The gD-A sequence, which encodes amino acids 253–283 (corresponding to amino acids 258–288, as incorrectly numbered by Watson et al., supra.) of the mature protein, was as follows:

5'-terminii) were 5'-phosphorylated with 5.6 units of T4 polynucleotide kinase (New England Nuclear) in 10 mM dithiothreitol (DTT), 1 mM ATP, 10 mM $MgCl_2$100 ng/ml spermidine, 50 mM Tris-HCl, pH 7.8 (total volume: 20 μl) for 30 min at 37° C. Additional T4 kinase (5.6 units) was then added and the reaction continued for 30 min at 37° C. The fragments (except for the 5' terminii) were combined, diluted to 40 μl with water followed by addition of 60 μl of 1M sodium acetate, 12 μl of 250 mM EDTA, and 5 μg of 1 mg/ml poly-dA. After heating for 5 min at 65° C., the 5' terminal pieces were added, followed by 420 μl of ethanol (100%). The solution was chilled for 20 min at −80° C., centrifuged, and the pellet was washed twice with ethanol (100%) and dried. The pellet was redissolved in water (18 μl), heated to 100° C. for 2 minutes and then cooled slowly over 1.5 hours to 25° C. in a water bath.

The annealed fragment pool was ligated in a reaction mixture containing T4 DNA ligase (New England Biolabs, 1200 units) 1 mM ATP, 10 mM DTT, 10 mM $MgCl_2$, 100

Processing Site

↓

```
ValProLeuAspLysArgLeuProProGluLeuSerGluThrProAsnAlaThrGln
 5'-CCTTGGATAAAAGATTGCCACCAGAATTGTCTGAAACCCCAAACGCTACCCAA
CATGGGAACCTATTTTCTAACGGTGGTCTTAACAGACTTTGGGGTTTGCGATGGGTT

ProGluLeuAlaProGluAspProGluAspSerAlaLeuLeuGluAspProOP OC
CCAGAATTGGCTCCAGAAGACCCAGAAGACTCTGCTTTGTTGGAAGACCCATGATAAG-3'
GGTCTTAACCGAGGTCTTCTGGGTCTTCTGAGACGAAACAACCTTCTGGGTACTATTCAGCT
```

The gD-B sequence, which encodes amino acids 8–23 (corresponding to amino acids 13–28, as incorrectly numbered by Watson et al., supra.) of the mature protein, was as follows:

ng/ml spermidine, and 50 mM Tris-HCl, pH 7.8 (30 μl). After 1 hour at 14° C., the reaction mixture was partially purified by preparative polyacrylamide gel (7%, native) electrophoresis. The DNA was removed from the appropri- Processing Site

↓

```
ValProLeuAspLysArgSerLeuLysMetAlaAspProAsnArgPheArgGlyLys
 5'-CCTTGGATAAAAGATCTTTGAAGATGGCTGACCCAAACAGATTCAGAGGTAAG
CATGGGAACCTATTTTCTAGAAACTTCTACCGACTGGGTTTGTCTAAGTCTCCATTC

AspLeuProOP OC
GACTTGCCATGATAAG-3'
CTGAACGGTACTATTCAGCT
```

The sequences each include a KpnI cohesive end at the 5'-end and a SalI cohesive end at the 3'-end. Coding for the mature secreted peptide begins after the LysArg processing site. The 5'-end of each sequence is a modification of the 3'-end of the naturally occurring α-factor secretory leader and processing signal sequence, where the modification consists of a deletion of three glu-ala pairs and a replacement of a leucine by a proline to create a KpnI site in the nucleotide sequence. The 3'-end of each sequence includes two translational stop codons, OP and OC.

Synthetic DNA fragments having the sequences just described were prepared by synthesizing overlapping ssDNA segments as described by Urdea et al. (1984) Proc. Natl. Acad. Sci. U.S.A. 80:7461–7465 using the phosphoramidite method of Beaucage and Carruthers (1981) Tetrahedron Lett. 27:1859–1862, and annealing and ligating under the following conditions.

The ssDNA fragments were joined as follows: 50 to 100 pmoles of each segment (except the two segments at the ate gel slice by electroelution and ethanol coprecipitation with poly-dA (5 μg).

After assembly, the synthetic gD-A and gD-B fragments were substituted into a KpnI/SalI digested bacterial cloning plasmid pAB114αEGF-24, which plasmid was prepared by cloning a mutagenized fragment of pYEGF-8 into pAB114 (see FIG. 1). The plasmids resulting from the insertion were designated pAB114αHS109 (gD-A) and pAB114αHS110 (gD-B).

The preparation of pAB114 was as follows: Plasmid pAB101 was obtained from the screening of a random yeast genomic library cloned in YEp24 (Fasiolo et al., 1981, J. Biol. Chem. 256:2324) using a synthetic 20-mer oligonucleotide probe (5'-TTAGTACATTGGTTGGCCGG-3')

homologous to the published α-factor coding region (Kurjan and Herskowitz, Abstracts 1981, Cold Springs Harbor meeting on the Molecular Biology of Yeasts, page 242). Plasmid AB11 was obtained by deleting the HindIII to SalI region of pBR322. An EcoRI fragment of pAB101 carrying the α-factor gene was then inserted into the unique EcoRI site in pAB11 to produce pAB112. Plasmid pAB112 was digested to completion with HindIII, and then religated at low (4 µg/ml) DNA concentration to produce plasmid pAB113 in which three 63 bp HindIII fragments were deleted from the α-factor structural gene, leaving only a single copy of mature α-factor coding region. A BamHI site was added to plasmid pAB11 by cleavage with EcoRI, filling in of the overhanging ends by the Klenow fragment of DNA polymerase, ligation of BamHI linkers and religation to obtain a plasmid designated pAB12. Plasmid pAB113 was digested with EcoRI, the overhanging ends filled in, and ligated to BamHI linkers. After digestion with BamHI, the resulting 1500 bp which carries the single copy of the α-factor gene fragment was gel-purified and ligated to pAB12 which had been digested with BamHI and treated with alkaline phosphatase to produce pAB114, which contains a 1500 bp BamHI fragment carrying the α-factor gene.

The preparation of pYEGF-8 was as follows: A synthetic sequence for human epidermal growth factor (EGF) was prepared and ligated to pAB112 (described above) which had been previously completely digested with HindIII and SalI to produce pAB201. The HindIII site lies within the 3'-end of the α-factor gene, and the EGF sequence was inserted using appropriate linkers. The resulting plasmid was designated pAB201.

Plasmid pAB201 (5 µg) was digested to completion with EcoRI and the resulting fragments were filled in with DNA polymerase I Klenow fragment and ligated to an excess of BamHI linkers. The resulting 1.75 kbp fragment was isolated by preparative gel electrophoresis, and approximately 100 ng of this fragment was ligated to long of yeast plasmid pC1/1 (described below) which had been previously digested to completion with restriction enzyme BamHI and treated with alkaline phosphatase. The ligation mixture of the 1.75 kbp fragment carrying the partial α-factor gene fused to the EGF gene and pC1/1 was used to transform *E. coli* HB101 cells, and transformants were selected based on ampicillin resistance. DNA from one ampicillin resistant clone (designated pYEGF-8) was used to transform yeast AB103 (genotype: MATα. pep 4-3, leu 2-3, leu 2-112, ura 3-52, his 4-580, cir°) cells, and transformants selected based on their leu$^+$ phenotype.

Plasmid pC1/1 is a derivative of pJDB219 (Beggs (1978) Nature 275:104) where the region derived from bacterial plasmid pMB9 has been replaced by pBR322. The pC1/1 plasmid carries genes for both ampicillin resistance and leucine prototrophy.

Plasmid pAB114αEGF-24 was generated by an in vitro mutagenesis procedure which deleted the sequences coding for the glu-ala processing region in the α-factor leader. Plasmid pAB114αEGF-24 was obtained as follows: a PstI-SalI fragment of pYEGF-8 containing the α-factor leader hEGF fusion was cloned in phage M13 and isolated in single-stranded form. A synthetic 36-mer oligonucleotide primer (5'-GGGGTACCTTTGGATAAAAGAAACTCCGACTCCGAA-3')

was used as a primer for the synthesis of the second strand using the Klenow fragment of DNA polymerase I. After fill-in and ligation at 14° C. for 18 hours, the mixture was treated with $S_1$ nuclease and used to transfect *E. coli* JM101 cells. Phage containing DNA sequences in which the glu-ala region was removed were located using $^{32}$P-labeled primer as a probe. DNA from positive plaques was isolated, digested with PstI and SalI, and the resulting fragment inserted into pAB114 (described above) which has been previously digested to completion with SalI, partially with PstI and treated with alkaline phosphatase. The resulting plasmid was designated pAB114αEGF-24.

Referring again to FIG. 1, the BamHI-BamHI fragment of pAB114αHS109 or pAB114αHS110 (1588 base pairs for gD-A and 1546 base pairs for gD-B) was excised and ligated into the unique BamHI site of pC1/1. The resulting expression vectors were designated pYHS109 for gD-A and pYHS110 for gD-B.

II.B. Expression of gD-A and gD-B polypeptides in yeast.

Plasmids pYHS109 and pYHS110 were both used to transform yeast strain AB103.1 (α, pep 4-3, leu 2-3, leu 2-112, ura 3-52, his 4-580, cir°) to leu prototrophy following the procedure of Hinnen et al. (1978) Proc. Natl. Acad. Sci. U.S.A. 75:1929–1933. The transformants were grown in 1 L cultures at 30° C. in buffered leucine-deficient media to saturation, corresponding to an absorbance of 5 at 650 nm . Yeast cell cultures were maintained at saturation for an additional 12 to 24 hrs with shaking at 30° C. The cultures were then harvested, the intact yeast cells pelleted by centrifugation at 3000 RPM, and the resulting supernatant media filtered through a 0.22µ Millipore filter. This fraction was then passed through a C18 reverse phase column, constructed from 8 Seppak units purchased from Waters. The bound material was eluted with 30 ml of 80% (v/v) acetonitrile, 0.1% (v/v) trifluoroacetic acid in water, evaporated to dryness with a Buchii RotoVap and redissolved in 1.6 ml of distilled water. This material was separated on a HPLC C18 column monitored at 210 nm. The peak corresponding to each respective peptide was collected and its identity confirmed by antigenicity. Each peptide reacted specifically in an ELISA assay using rabbit polyclonal antisera which had been raised against a chemically synthesized gD-B peptide or partial gD-A peptide (residues 256 through 271 of the sequence as shown in II.A.) purchased from Vega Biochemicals. Expression levels, as determined by spectrophotometric measurements of HPLC purified peptides, were on the order of 7.6 mg of gD-A per liter of yeast culture ($OD_{650}$=5) and 0.6 mg of gD-B per liter of yeast culture ($OD_{650}$=5). These results demonstrate the feasibility of expressing a relatively short portion or fragment of a protein and its secretion from yeast cells using an α-factor expression vector.

II.C. Construction of yeast vectors for high level intracellular expression usfng fragments of the naturally occurring gD1 gene.

Nucleotide fragments from the naturally occurring gD gene expressing gD of HSV-1 (gD-1) were also expressed intracellularly in yeast under control of the GAPDH promoter and terminator. A library of EcoRI fragments of HSV-1, strain Patton, cloned into the EcoRI site of pBR322, was made by Dr. Richard Hyman, Hershey Medical Center, Hershey, Pa. The gD is entirely contained within a 2.9 kb SacI fragment within the EcoRI fragment of one clone (clone H) isolated from the HSV-1 library. Clone H was obtained from Dr. Hyman, the 2.9 kb fragment was purified by gel electrophoresis and was used for the construction of several expression vectors which differ in the size of the gD fragment cloned and/or the synthetic linkers used in the 5' or 3' ends of the gD fragmentS. FIG. 2 illustrates the protein coding region (boxed region) and the fragments used for the construction of yeast expression vectors pYHS115, pYHS116, pYHS117, pYHS118 and pYHS119. A description of the construction of each plasmid follows.

II.C.1. Construction of pYHS115.

Plasmid pYHS115 contains the gD gene in a GAPDH expression cassette cloned into the BamHI site of pC1/1 (described hereinabove).

The GAPDH expression cassette was constructed as follows. Three fragments were prepared (as described in detail below):

(a) A BamHI-HindIII fragment (1407 bp) containing 346 bp of pBR322 and 1061 bp of the GAPDH promoter;

(b) A HindIII-SalI fragment (1430 bp) containing the gD gene; and (c) A SalI-BamHI fragment (900 bp) containing the GAPDH terminator.

These fragments were ligated together and the mixture was digested with BamHI. The 3.7 Kb resulting cassette was isolated by gel electrophoresis and ligated to BamHI cut, alkaline phosphatase-treated pC1/1 (FIG. 3).

Fragment (a) was prepared by completely digesting pGAP347 (described below) with BamHI followed by partial digestion with HindIII. The resulting 1407 bp fragment containing 346 bp of pBR322 and 1061 bp of the GAPDH promoter was isolated by gel electrophoresis.

Construction of pGAP347 was as follows (see copending application Ser. No. 468,589, filed Feb. 22, 1983): PolyA$^+$ RNA was isolated from S. cerevisiae yeast strain A364A. Double-stranded cDNA was synthesized using AMV reverse transcriptase and E. coli DNA polymerase I. Poly-dC-tails were added to the double-stranded cDNA molecule using deoxynucleotide terminal transferase. Poly-dC-tailed cDNA was annealed to poly-dG-tailed pBR322 and used to transform E. coli HB101. 1000 transformants were screened by colony hybridization to labeled PolyA$^+$ RNA, and a subset further examined by restriction endonuclease mapping, and DNA sequencing. Three clones containing GAPDH sequences were isolated from the pool. One clone (pcGAP-9) contained an insert of about 1200 base pairs and was used for further work.

A yeast gene library was prepared by inserting fragments obtained after partial digestion of total yeast DNA with restriction endonuclease Sau3A in lambda phage Charon 28, according to Blattner et al. (1977) Science 196:161–169. Several fragments containing yeast GAPDH coding sequences were isolated by screening the phage library with labeled DNA from pcGAP-9. The yeast GAPDH gene of one of these clones was subcloned in pBR322 as a 2.1 kb HindIII fragment (pGAP-1). The GAPDH promoter region was isolated from these clones. A HhaI-HindIII fragment of about 350 bp containing the 3' portion of the promoter was obtained by: a) digestion of pGAP-1 with HinfI to generate an approximately 500 bp segment which includes the 3' part of the promoter and a region encoding the N-terminal amino acids of GAPDH; b) resection with Bal31 to yield a 400 bp fragment lacking the GAPDH coding region (3'-terminus one base upstream from the ATG initiator codon); c) addition of HindIII linkers; and d) cleavage with HhaI. A second HindIII-HhaI fragment of about 700 bp containing the 5' portion of the promoter was isolated from pGAP-1, ligated to the 350 bp HhaI-HindIII fragment and treated with HindIII. The resulting 1061 bp HindIII fragment was isolated by gel electrophoresis and cloned in HindIII digested, alkaline phosphatase treated pBR322 to produce pGAP347.

Fragment (b) was obtained as follows. Clone H, isolated from the HSV-1 Patton library was digested with SacI. A 2.9 Kb SacI fragment was purified by gel electrophoresis and subsequently digested with HindIII and NruI. The 1430 bp HindIII-NruI fragment containing the gD gene (FIG. 3) was purified by gel electrophoresis, ligated to NruI-SalI adaptors of the following sequence:

```
5'-TGATAAG-3'
   ACTATTCAGCT
``` and digested with SalI.

Fragment (c) was obtained as follows. A 900 bp fragment containing the GAPDH terminator was obtained by BamHI and SalI digestion of pUH28 (described under "Construction of pYHS117") and purification by gel electrophoresis.

II.C.2. Construction of pYHS116 pYHS116 contains a gD gene fragment which has a 600 bp deletion at the 5' end of the coding region that comprises most of the signal sequence coding region. To construct pYHS116, two fragments were obtained:

(a) A BamHI-HindIII fragment (1407 bp) containing 346 bp of pBR322 and 1061 bp of the GAPDH promoter. This fragment was obtained as described under "Construction of pYHS115."

(b) A NcoI-BamHI fragment (2150 bp) containing the partial gD gene followed by the GAPDH terminator. This fragment was obtained by BamHI/NcoI digestion of pYHS115 (described previously) and purification by gel electrophoresis. A HindIII-NcoI chemically synthesized adaptor of the following sequence

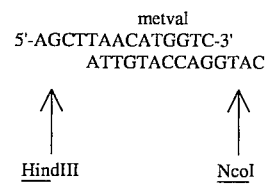

was ligated to the fragment. This adaptor provides for the first two codons (met and val) fused in the correct reading frame to the partial gD.

Fragments (a) and (b) were ligated together and subsequently digested with BamHI. The resulting 3.5 Kb cassette was isolated by gel electrophoresis and ligated to BamHI cut. alkaline phosphatase treated pC1/1.

II.C.3. Construction of pYHS117

Plasmid pYHS117 contains the same partial gD gene clone in pYHS116, fused in reading frame to 7 extra codons at the 5'-end, which code for the first 7 amino acids of the GAPDH structural gene. To construct pYHS117 two fragments were obtained.

(a) An NcoI-SalI digested vector (6.8 Kb) comprising pBR322 sequences, the GAPDH promoter fused to the first 7 codons of the structural gene and the GAPDH terminator. This vector was prepared by NcoI digestion of pUH28 (described below), followed by a partial digestion with SalI and purification by gel electrophoresis.

(b) An NcoI-SalI fragment (1430 bp) containing a partial gD gene. This fragment was obtained by BamHI-SalI digestion of pYHS115 (described previously in Section II.C.1.) and purification by gel electrophoresis.

These two fragments were ligated together to yield a pBR322 derived vector which contains a partial gD gene fused in reading frame to the 7 first codons of GAPDH gene, flanked by the GAPDH promoter in its 5' end and by the GAPDH terminator in its 3' end. The gD expression cassette was obtained by digesting this plasmid with BamHI and purifying a 3.4 Kb fragment by gel electrophoresis. This fragment was ligated to BamHI digested, alkaline phosphatase treated pC1/1 to produce pYHS117.

Plasmid pUH28 contains the coding and 3' noncoding regions of the hepatitis B surface antigen (HBsAg) gene fused in incorrect reading frame to the first 7 codons of the GAPDH structural gene. This fusion is flanked in its 5' end by the GAPDH promoter and in its 3' end by part of the GAPDH coding region followed by the GAPDH terminator. This plasmid was constructed so as to have an NcoI site at the 3' end of the first 7 codons of the GAPDH gene with the following sequence:

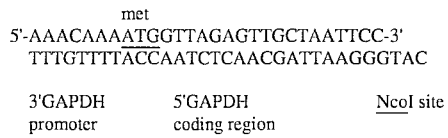

When this NcoI end is ligated to the partial gD fragment (b, described above) the correct reading frame for the gD protein is regenerated. The SalI site used in the preparation of fragment a (described above) is at the 5' region of the GAPDH terminator. Therefore, a deletion of the sAg coding plus non-coding regions and GAPDH coding region was obtained by digesting pUH28 with NcoI and partially with SalI.

The construction of pUH28 involves cloning of a fragment that contains the HBsAg coding and 607 bp of 3' non-coding region prepared from pHBS5-3 Hae2-1 (described below) into the GAPDH containing vector pGAP'$_2$ (described below). To prepare the fragment, pHBS5-3 Hae2-1 was linearized by PstI digestion, partially digested with NcoI and a PstI-NcoI fragment of 1.9 Kb containing pBR322 sequences, HBsAg coding and 3' sequences was purified by gel electrophoresis. This fragment was subsequently digested with EcoRI and a 1.2 Kb NcoI-EcoRI fragment containing the HBsAg coding and 3' non-coding regions was purified by gel electrophoresis. Plasmid pGAP'$_2$ was linearized with XbaI and treated with Bal31 to remove approximately 100 bp. The plasmid was subsequently digested with NcoI and a vector fragment of about 9 Kb was purified by gel electrophoresis. The NcoI ends of the vector and the 1.2 Kb NcoI-EcoRI fragment encoding HBsAg were ligated. The recessed end was filled in with Klenow and the resulting blunt end was ligated to the blunt end of the vector obtained by Bal31 digestion to produce pUH28.

pHBS5-3 Hae2-1 is a plasmid that contains the HBsAg coding region and 607 bp of 3' flanking sequences. This plasmid is a derivative of pHBS5-3 which contains the same insert but only 128 bp of 3' untranslated region instead of 607 bp. Plasmid pHBS5-3 has been previously described in copending application, Ser. No. 609,540, filed May 11, 1984, (pp. 13–14), pHBS5-3 Hae2-1 was constructed as follows. The HBV genome (3.2 kb) was excised from pHB-3200 (Valenzuela et al., 1979, Nature, 280:815–819) by restriction digestion with EcoRI. The 3.2 kb fragment was purified by gel electrophoresis and was recircularized by ligation of the EcoRI sticky ends. This closed HBV genome was digested with HaeII, which cuts in the 3' non-coding region. Recessed ends were filled in with Klenow and HindIII linkers were ligated. The DNA was cut with HindIII and subsequently with XbaI, which has a single site in the HBS coding region. A 1.2 kb XbaI-HindIII fragment containing 586 base pairs of the coding sequence of HBV and 607 base pairs of the 3' non-coding region was isolated by gel electrophoresis. This fragment was cloned into pHBS5-3 previously cut with XbaI and HindIII and treated with alkaline phosphatase, to yield pHBS5-3 Hae2-1.

pGAP-2 is a pBR322 derived vector which contains a BamHI insert that has the GAPDH coding sequence, 5' and 3' flanking regions. There are two XbaI sites in this plasmid: one in the coding region and one in the 3' flanking sequences. pGAP-2' is a derivative of pGAP-2 in which the XbaI site present in the 3' flanking region has been eliminated. For this purpose, 50 μg of pGAP-2 were partially digested with XbaI, treated with Bal31 to remove 25 base pairs per end, and ligated. The plasmids were used to transform E. coli HB101 and the transformants were selected for loss of the XbaI site in the 3' flanking region.

II.C.4. Construction of pYHS118

This vector contains a partial gD gene with deletions in two regions: a 600 bp deletion in the 5'-end coding region which comprises most of the signal sequence coding region and a 1300 bp deletion in the 3'-end coding region which includes most of the anchor sequence coding region. It also contains 7 extra codons from the GAPDH gene coding region fused in reading frame at the 5' end of the gD gene, similar to pYHS117. Plasmid pYHS118 was constructed as follows. pYHS115 was digested with NcoI and SalI, the resulting 1430 bp fragment containing the partial gD was purified by gel electrophoresis and submitted to digestion with NarI (FIG. 2). The two resulting fragments (fragment a: 873 bp containing 5' end and fragment b: 411 bp containing 3' end) were independently isolated by gel electrophoresis. Fragment b was subsequently digested with Sau96A to yield three fragments which were separated by gel electrophoresis. The 87 bp NarI-Sau96A fragment was recovered from the gel and was ligated to Sau96A-SalI synthetic adaptors of the following sequence:

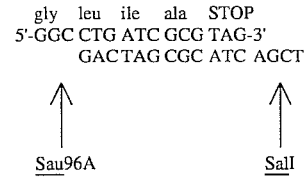

The NarI-(Sau96A)SalI fragment (102 bp) was digested with SalI, purified by gel electrophoresis and ligated with fragment a (previously described). The resulting NcoI-SalI fragment (975 bp) was ligated to NcoI-SalI digested and gel purified pUH28 as described under "Construction of pYHS117." The resulting pBR322 derived vector was digested with BamHI and a 3.1 Kb fragment containing the gD expression cassette was purified by gel electrophoresis. This cassette was ligated to BamHI digested, alkaline phosphatase treated pCl/1 to produce pYHS118.

II.C.5. Construction of pYHS119

This vector contains a partial gD gene with deletions in two regions: a 600 bp deletion in the 5' end coding region which comprises most of the signal sequence coding region and a 2400 bp deletion in the 3' end coding region which includes all the anchor sequence coding region and about 700 bp upstream of the anchor sequence. It also contains 7 extra codons from the GAPDH gene coding region fused in reading frame at the 5' end of the gD gene, as pYHS117 and pYHS118. Plasmid pYHS119 was constructed as follows. pYHS115 was digested with NcoI and SalI, the resulting 1430 bp fragment containing the partial gD was purified by gel electrophoresis and subsequently digested with NarI. The 873 bp NcoI-NarI fragment was isolated by gel electrophoresis. A synthetic adaptor of the following sequence:

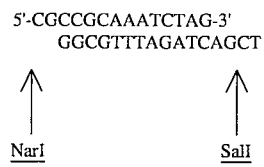

```
5'-CGCCGCAAATCTAG-3'
   GGCGTTTAGATCAGCT
      ↑           ↑
      |           |
     NarI        SalI
``` which provides complementary nucleotides to the NarI 5' overhang, 3 codons in reading frame, a stop codon and a 5' overhang of SalI, was ligated to the 873 bp NcoI-NarI fragment then digested with SalI. The resulting NcoI SalI fragment was ligated to pUH28 which had been previously completely digested with NcoI and partially digested with SalI and purified by gel electrophoresis as described under "Construction of pYHS117." The resulting pBR322 derived vector was digested with BamHI and a 2.2 Kb fragment containing the gD expression cassette was purified by gel electrophoresis. This cassette was ligated to BamHI digested, alkaline phosphatase treated pCI/1 to produce pYHS119.

II.D. Synthesis of gD1 from vectors containing partial or complete gD1 gene.

Plasmids pYHS115, 116, 117, 118 and 119 were used to transform yeast strain AB103.1 (α, pep 4-3, leu 2-3, leu 2-113, ura 3-52, his 4-580, cir°) following the procedure of Hinnen et al., (supra.). The transformants were grown to an $OD_{650}=3$ at 30° C. in YEPD media. The cultures were then harvested by pelleting the yeast cells at 3000 RPM. Cells were spheroplasted with zymolyase and subsequently osmotically lysed in a hypotonic solution. Membranes were spun down in an eppendorf centrifuge, and the pellet was solubilized in 0.1% SDS with protease inhibitors for 16 hours at 4° C. The suspension was centrifuged and total protein, as well as gD specific protein, was determined in both soluble and insoluble fractions. Expression of the gD gene in each of the above described constructions was detected by Western Blot hybridization (Towbin et al., 1979, Proc. Natl. Acad. Sci. U.S.A. 76:4350). For this purpose protein samples were submitted to SDS-polyacrylamide gel electrophoresis (Laemmli (1970) Nature 227:680) and electroblotted onto nitrocellulose filters (Towbin et al. supra.). The filter was preincubated with goat serum and subsequently treated with a rabbit polyclonal antibody raised against HSV-1 (Dako). The filter was then incubated with a second goat anti-rabbit antibody conjugated with horseradish peroxidase (Boehringer-Mannheim) and finally it was incubated with horseradish peroxide color development reagent (Bio-Rad) and washed. The results indicate that immunoreactive material is being synthesized in yeast AB103.1 strain transformed with the gD expression vectors, with the exception of transformants containing pYHS115. In all other cases, gD protein corresponds to 0.1 to 0.5% of total yeast cell protein.

According to the present invention, novel DNA constructs are provided for expressing high levels of a polypeptide which is immunologically cross-reactive with Herpes Simplex virus glycoprotein D. Such expression is carried out in yeast. The genes expressed may be natural, synthetic or a combination of both, and secretion facilitates recovery of the gD gene product. Expression of both short, synthetic fragments corresponding to a portion of the gD protein and long, natural fragments corresponding to the entire gD protein has been demonstrated. Both approaches yield polypeptides that are immunologically reactive with antisera raised against natural gD protein.

IV. Vaccine Trials

The gD protein was prepared from *Saccharomyces cerevisiae* by cloning a portion of the gD gene encoding amino acids −5 through +339 from the HSV-1 strain Patton into plasmid pYHS118 (previously described in Section II.C.4). Expression of the gD gene in this vector is directed by the GAPDH transcriptional promoter and terminator signals. The gD protein was purified from yeast cell lysates by differential solubilization and was judged 80% homogenous by SDS polyacrylamide gel electrophoresis and Western blot analysis. Vaccines containing a mixture of HSV glycoproteins were prepared from HSV-1 strain Patton or HSV-2 strain 333 infected Vero cells by lentil lectin sepharose chromatography using the method of Respess et al. J. Virol. Methods 8:27 (1984). These mixtures contained for HSV-1, approximately 36% gB1 and 26% gD1, and for HSV-2, approximately 22% gB2 and 4.5% gD2, as percent of total protein. In addition the mixtures contained as well as high concentrations of gC, lower amounts of gE and gG plus a mixture of unidentified HSV and Vero cell proteins.

IV.A. Humoral immunity in mice

Outbred female Swiss Webster mice (Simonsen) were immunized on day 1 with a 1:1 mixture of recombinant vaccine preparation and complete Freund's adjuvant. One half the dose was administered subcutaneously, the other half intraperitoneally. The mice received 20 μg recombinant gD1 protein synthesized in yeast. Mice were boosted on day 20 with the same dose and vaccine preparation, but incomplete Freund's adjuvant was used to make the emulsion. They were bled by cardiac puncture on day 28. A mixture of HSV-1 glycoproteins prepared by lectin affinity purification served as a positive vaccine control, and a recombinant feline leukemia envelope B protein was used as a negative control. A second boost was given on day 41 and animals were bled again on day 53. Beta from the mouse bleeds were collected and assayed for antibody levels by ELISA and plaque reduction neutralization assay. The results of this experiment are summarized in Table 1 below.

TABLE 1

Experiment 1: Humoral Immunity in Mice

| Animal | Immunogen | Dose | ELISA Titer[a] | Neutralization Titer[b] |
|---|---|---|---|---|
| | | BLEED #1 | | |
| 1 | recombinant gD | 20 μg | 1:284 | <1:20 |
| 2 | recombinant gD | 20 μg | 1:77 | <1:20 |
| 3 | recombinant gD | 20 μg | 1:142 | <1:20 |
| 6 | env B | 20 μg | <1:10 | <1:20 |
| 7 | total herpes glycoproteins | 20 μg | 1:175 | 1:125 |
| | | BLEED #2 | | |
| 1 | recombinant gD | 20 μg | 1:250 | n.d.[c] |
| 2 | recombinant gD | 20 μg | 1:50 | n.d. |
| 3 | recombinant gD | 20 μg | 1:81 | n.d. |
| 6 | env B | 20 μg | <1:10 | n.d. |
| 7 | total HSV glycoproteins | 20 μg | 1:1468 | n.d. |

[a]ELISA with 20 μg/ml total HSV-1 (Patton) glycoproteins as antigen. 50% endpoint.
[b]Plaque reduction neutralization assay with complement. HSV-1 (McIntyre). 50% endpoint.
[c]Not done.

IV.A.2. Protection of mice against virus challenge

The in vivo response of mice to the vaccine candidates was also examined by challenging immunized animals with a lethal dose of virus. Female Swiss Webster mice were immunized with the vaccine candidates. The first injections were done using 20 μg recombinant gD mixed in an equal volume of complete Freund's adjuvant. One half the dose was given intraperitoneally, the other half subcutaneously on day 1. Mice were boosted 2 and 4 weeks later in the same manner with incomplete Freund's adjuvant in the emulsion. Control animals received 20 μg of lectin purified total HSV glycoproteins previously described or 23 μg of a control yeast plus CHO cell extract. Mice were bled one week after the final boost by cardiac puncture. Sera were collected and assayed for antibody titers by ELISA. Animals were challenged 15 days later with $3.25 \times 10^8$ pfu of HSV-1 (Patton) (2 $LD_{50's}$) given intraperitoneally. They were monitored for a 14 day time period for the appearance of clinical signs or morbidity. Mice surviving the virus challenge were observed for 10 additional days at which time they were bled and the sera examined by ELISA. The results of this experiment are summarized in Table 2 below.

TABLE 2

Experiment 2: Protection of mice against virus challenge

| Group | Animal | Immunogen | Dose | ELISA Titer[a] | % Survival | ELISA Titer[b] |
|---|---|---|---|---|---|---|
| 1 | A | recombi- | 20 μg | 1:98 | 40 (2/5) | |
|   | B | nant gD |       | 1:146 |         | |
|   | C |         |       | n.d.[c] |       | 1:862 |
|   | D |         |       | 1:355 |         | 1:1514 |
|   | E |         |       | 1:106 |         | |
| 3 | A | total HSV | 20 μg | 1:2339 | 100 (4/4) | 1:1928 |
|   | B | glyco-   |       | 1:172 |           | 1:965 |
|   | C | proteins |       | 1:2660 |          | 1:5488 |
|   | D |         |       | 1:2883 |          | 1:3026 |
| 4 | A | control | 23 μg | <1:25 | 20 (1/5) | 1:734 |
|   | B | cell    |       | 1:85  |          | |
|   | C | extracts |      | 1:51  |          | |
|   | D |         |       | <1:25 |          | |
|   | E |         |       | <1:25 |          | |

[a]ELISA with 10 μg/ml total HSV-1 (Patton) glycoproteins as antigen, 50% endpoint.
[b]Percent of mice surviving 14 days after challenge. (Number of surviving mice over total number.)
[c]Not done. No blood was obtained from this mouse for assay.
[d]Sera tested from mice surviving virus challenge.

IV.B. Protection of guinea pigs against initial and recurrent genital herpes

Eighty, 350 to 400 gram female Harltey guinea pigs (Charles River Breeding Laboratory, Wilmington, Mass.) were immunized in the hind footpads 60 and again 30 days prior to intravaginal inoculation with 5.7 $\log_{10}$ pfu HSV-2, MS strain (Stanberry et al (1985) Intervirology 24:226. Animals were immunized as follows: Group I—unimmunized control; Group II—control yeast and CHO cell protein extracts (32 μg) plus complete Freund's adjuvant (CFA); Group III—HSV-1 gD (10 μg) plus CFA; Group IV—HSV-1 gD (100 μg) plus CFA; Group VI—HSV-1 glycoprotein mixture (50 μg) without adjuvant; Group VII—HBV-1 glycoprotein mixture (50 μg) plus CFA; Group VIII—HSV-2 glycoprotein mixture (50 μg) without adjuvant: Group IX—HSV-2 glycoprotein mixture (50 μg) plus CFA. All vaccines were adjusted to a total volume of 0.1 ml and administered with an equal volume of adjuvant of 0.9% saline.

Figure 4D:
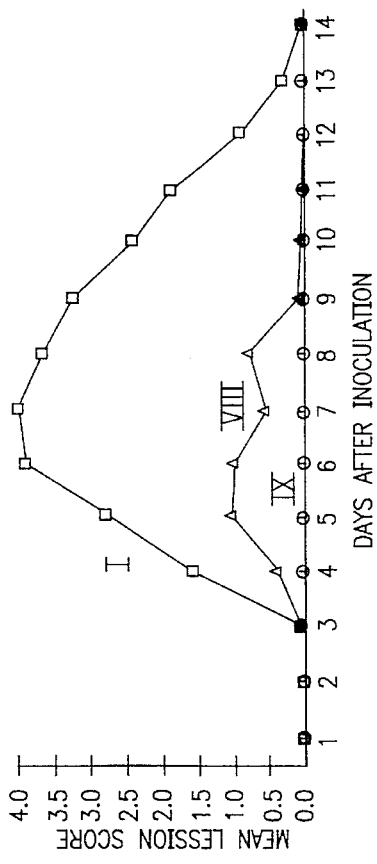
Figure 4A:
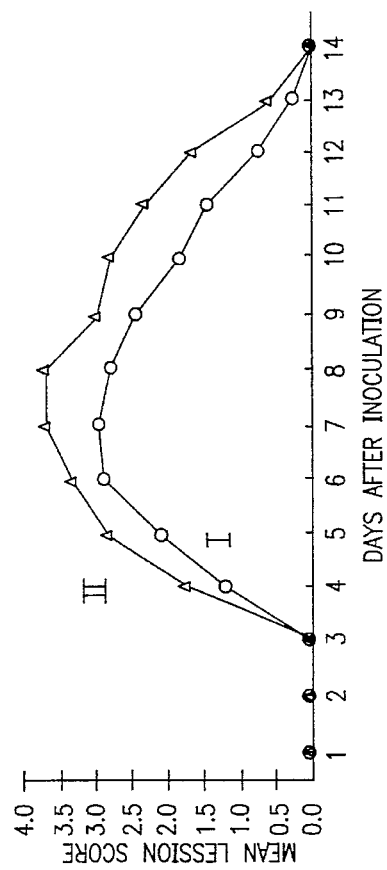
Figure 4C:
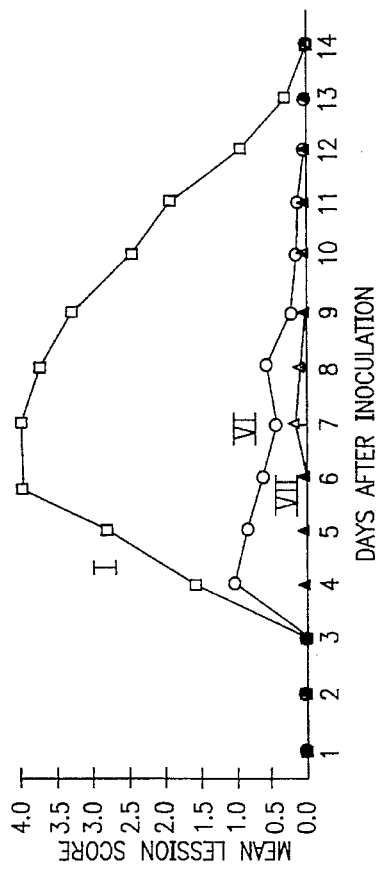

The course of initial genital HSV-2 infection was evaluated by genital skin lesion scores, incidence of urinary retention and titer of virus in vaginal swab samples (Stanberry et al. (1982) J. Infect. Dis. 146:397 (1982)). The following skin lesion score was used: 0=no disease; 1=redness or swelling; 2=a few small vesicles; 3=several large vesicles; 4=several large ulcers with maceration. The clinical course of initial infection is summarized in Tables 3 and 4 and FIG. 4. Compared to the unimmunized and cell extract control groups the frequency of both skin disease and urinary retention was reduced in all vaccinated groups of animals except those receiving the lower (10 μg) dose of HSV-1 gD. The recombinant glycoprotein preparations reduced the severity of genital skin disease by 90% for gD (100 μg dose) while the glycoprotein mixtures administered with adjuvant completely eliminated any manifestations of skin disease.

It was further observed that viral replication in the genital tract was also altered by prior immunization with a glycoprotein preparation (Table 4, FIG. 5). In the tests reported on FIG. 5, vaginal swab samples were collected with calcium alginate swabs and placed in 1 ml Eagles Basal Medium containing 100 units of penicillin, 50 μg of streptomycin, 50 μg of gentamicin, and 2.5 μg of amphotericin B. Samples were stored at −70° C. The concentration of virus was determined by plaque assay on rabbit kidney cells under a 0.5 percent methylcellulose overlay. The peak virus titer in vaginal secretions was significantly reduced in all treatment groups except low dose (10 μg) gD ($p<0.01$). Guinea pigs receiving the mixture of HSV-1 or HSV-2 glycoproteins plus CFA had peak titers less than 0.01% of control values. Likewise, the magnitude of viral replication throughout initial infection as represented by the area under the log virus titer-day curve (FIG. 5) was also significantly lower for these groups ($p>0.01$).

TABLE 3

Severity of primary infection in guinea pigs challenged with HSV-2

| Group | Immungen | Score[a] | Range | Number of Animals |
|---|---|---|---|---|
| 1 | Control, yeast plus CHO cell extracts plus CFA | 3.7 ± 0.1 | 3–4 | 10 |
| 2 | 10 μg recombinant gD plus CFA | 1.3 ± 0.3 | 0–3 | 8 |
| 3 | 100 μg recombinant gD plus CFA | 0.2 ± 0.2 | 0–1 | 7 |
| 6 | 50 μg total HSV-1 glycoproteins plus CFA | 0.0 | N/A | 7 |
| 7 | 50 μg total HSV-1 glycoproteins | 0.4 ± 0.1 | 0–1 | 7 |
| 8 | 50 μg total HSV-2 glycoproteins plus CFA | 0.0 | N/A | 8 |
| 9 | 50 μg total HSV-2 glycoproteins | 0.4 ± 0.2 | 0–1.5 | 8 |
| 10 | Control, no treatment | 3.0 ± 0.3 | 0–4 | 16 |

[a]Seven days post challenge.

TABLE 4

Clinical and virologic couse of initial genital Herpes Simplex virus type 2 infection in guinea pigs

| Group | Vaccine[a] | Concentr. μg | Incidence of Skin Lesions | Skin Lesion Severity[b] | Incidence of Urinary Retention | Incidence of Viral Replication[c] | Magnitude of Viral Replication[d] |
|---|---|---|---|---|---|---|---|
| I | Unimmunized | — | 16/16 | 18.9 | 16/16 | 16/16 | 29.0 |
| II | Cell extract control | 32 | 10/10 | 25.7 | 10/10 | 10/10 | 30.3 |
| III | HSV-1 gD | 10 | 8/8 | 6.1 | 8/8 | 8/8 | 26.0 |
| IV | HSV-1 gD | 100 | 3/7 | 1.1 | 2/7 | 7/7 | 21.8 |
| VI | HSV-1 total glycoproteins | 50 | 5/7 | 3.0 | 4/7 | 7/7 | 19.9 |
| VII | HSV-1 total glycoproteins | 50 | 0/7 | 0 | 0/7 | 7/7 | 4.1 |
| VIII | HSV-2 total glycoproteins | 50 | 6/10 | 3.5 | 3/10 | 10/10 | 16.9 |
| IX | HSV-2 total glycoproteins | 50 | 0/8 | 0 | 0/8 | 8/8 | 3.3 |

[a]Groups II, III, IV, VII, IX administered with Complete Freund's Adjuvant: Groups, I, VI, VIII administered without adjuvant.
[b]Calculated as the area under the mean lesions score day curve.
[c]Defined by recovery of virus from vaginal swab sample on at least two occasions 24 hours apart.
[d]Calculated as the area under the mean virus titer-day curve.

It has been previously reported that prior HSV infection also reduced the magnitude of viral replication in the genital tract resulting from intravaginal HSV-2 rechallenge (Stanberry, et al. (1986) J. Infect. Dis. 153:1055). However, prior immunization with the HSV-1 or HSV-2 glycoprotein mixture plus adjuvant resulted in a greater reduction in the magnitude of viral replication after HSV-2 inoculation (Table 4) than was observed in animals intravaginally rechallenged with HSV-2 after recovery from initial genital HSV-2 infection (mean area under the log virus titer-day curve presented in FIG. 1 of above reference: initial infection=36.5±1.5; rechallenge= 17.0±2.4 (p<0.01)). These data suggest that immunization with a subunit vaccine may potentially provide greater protection from HSV infection than that elicited by previous infection. This study, as well as that by Berman et al. (1984) Science 227:1490, indicates that prior immunization with HSV glycoprotein vaccines provides substantial protection against the clinical manifestations of intravaginal HSV-2 challenge in guinea pigs. As shown here, recombinant HSV-1 gD affords similar protection to that provided by the HSV-1 or HSV-2 glycoprotein mixture. Our data indicates, however, that the greatest protection against vaginal HSV-2 replication was provided by immunization with the glycoprotein mixtures and that the effects were greatly enhanced by the presence of adjuvant.

The effect of immunization prior to initial infection on the subsequent pattern of recurrent genital HSV-2 infection between days 15 to 62 post intravaginal challenge is summarized in Table 5. It has been previously reported that all animals surviving initial infection exhibit spontaneous recurrent herpetic lesions on the external genital skin (Stanberry et al. (1985) (supra)). This study demonstrates that immunization with HSV glycoprotein vaccine prior to HSV-2 challenge can protect animals from developing recurrent genital HSV-2 infection. For example, 42% of gD immunized animals did not exhibit recurrent herpetic disease while 57% and 94% of guinea pigs immunized with the HSV-1 or HSV-2 glycoprotein mixture with adjuvant were protected from developing recurrent herpetic infections. These observations indicate that administration of a subunit HSV glycoprotein vaccine may have a very substantial impact on the natural history of recurrent herpetic disease.

The antibody response to HSV-1 and HSV-2 antigens after immunization and intravaginal HSV-2 challenge is shown in Table 6. Sera were collected from animals 30 days after the second immunization, but prior to infection (day 0), and again 30 days after intravaginal HSV-2 inoculation (day 30) and were assayed for anti-HSV antibodies by both ELISA and virus neutralization plaque reduction assays. The ELISA method was a modification of the method of Morahan et al. (1981) Infect. Immun. 32:180 utilizing either the lectin purified HSV-1 or HSV-2 glycoprotein mixture as the coating antigen and assigning a 50% endpoint as the ELISA titer. The plaque reduction assay was similar to that described by Bernstein et al. J. Gen Virol. (in press) except that all sera were tested in the presence of exogenously added complement. All animals seroconverted (Table 6) following infection but the magnitude of the antibody response by day 30 was significantly greater in animals immunized with the HSV-1 or HSV-2 glycoprotein mixture plus adjuvant than in the unimmunized controls (p<0.001). It was apparent that animals with pre-existing HSV antibodies (seropositive on day 0) had milder initial disease and less frequent recurrent infections than seronegative animals. When one controlled for the variable introduced by treatment group, analysis of the data revealed the total number of days animals experienced recurrent herpetic lesions was negatively related to the antibody titer prior to intravaginal HSV-2 challenge (day 0) (p=0.04 by analysis of covariance). However, similar analysis failed to demonstrate any correlation between antibody response on either day 0 or day 30 and any measure of the severity of initial infection (i.e., peak lesion score, area under the lesion score-day curve, incidence or duration of urinary retention). Interestingly, the antibody titers on day 30 (but not day 0) were negatively correlated with the peak virus titer in vaginal secretions (p=0.003) and the area under the virus titer-day curve (FIG. 4b) (p=0.007 by analysis of covariance).

TABLE 5

Effect of viral glycoprotein immunization on the pattern of recurrent genital Herpes Simplex virus type 3 infection in guinea pigs[a]

| Vaccine | Adjuvant[b] | Animals with Recurrent Lesions | Lesion Days per Animal[c,d] | Episodes per Animal[c,e] | Lesion Days/Episode per Animal[f] |
|---|---|---|---|---|---|
| Unimmunized | No | 4/4 | 16.3 ± 1.9 | 7.8 ± 0.9 | 2.1 ± 0.2 |
| HSV-1 gD (10 µg) | Yes | 5/5 | 7.6 ± 2.2 | 4.6 ± 1.2 | 1.7 ± 0.1 |
| HSV-1 gD (100 µg) | Yes | 4/7 | 5.9 ± 2.0 | 3.3 ± 1.6 | 1.7 ± 0.3 |
| HSV-1 glycoproteins (50 µg) | No | 7/7 | 9.9 ± 2.4 | 5.6 ± 0.9 | 1.6 ± 0.2 |
| HSV-1 glycoproteins (50 µg) | Yes | 3/7 | 0.7 ± 0.4 | 0.6 ± 0.3 | 1.3 ± 0.3 |
| HSV-2 glycoproteins (50 µg) | No | 8/8 | 8.9 ± 3.2 | 3.4 ± 1.0 | 1.9 ± 0.4 |
| HSV-2 glycoproteins (50 µg) | Yes | 1/8 | 0.5 ± 0.5 | 0.5 ± 0.5 | 1.0 ± 0 |

[a]Animals were immunized in the hind footpad 60 and again 30 days prior to intravaginal HSV-2 inoculation. After recovery from initial infection, animals were examied daily from day 15 through day 62 post inoculation for evidence of recurrent herpetic lesions.
[b]Complete Freund's adjuvant.
[c]Mean ± standard error, calculated using all animals.
[d]Days when a recurrent lesion was observed.
[e]An episode of recurrent disease was defined as lesion day(s) preceded and followed by a day without any lesion.
[f]Mean ± standard error, calculated using only animals with recurrent lesions.

Guinea pigs immunized with HSV glycoproteins were protected against the clinical manifestations of initial HSV-2 genital infection and experienced a reduced incidence, frequency and duration of recurrent herpetic disease. The extent of protection was influenced by the nature of the glycoprotein vaccine, the immunizing dose and the co-administration of adjuvant.

Although the foregoing invention has been described in some detail by way of illustration and example for purposes of clarity of understanding, it will be obvious that certain changes and modifications may be practiced within the scope of the appended claims.

What is claimed is:

1. A method for alleviating recurrent Herpes Simplex Virus (HSV) infection in a human comprising vaccinating said human subsequent to HSV infection with an amount of a vaccine effective to produce an immune response in said human, said vaccine consisting essentially of an adjuvant and a protein selected from the group consisting of glycoprotein D (gD) of HSV and a C-terminally truncated form of HSV gD which lacks all or a portion of the anchor sequence coding region.

2. The method of claim 1, wherein said protein is recombinantly produced.

3. The method of claim 2, wherein the protein is a C-terminally truncated form of HSV gD which lacks all or a portion of the anchor sequence coding region.

4. The method of claim 1, wherein said protein is of HSV type 1.

5. The method of claim 1, wherein said adjuvant is selected from the group consisting of aluminum hydroxide, muramyl dipeptide, and muramyl peptide derivatives.

* * * * *